United States Patent [19]

LaPointe et al.

[11] Patent Number: 5,721,185

[45] Date of Patent: Feb. 24, 1998

[54] HOMOGENEOUS OLEFIN POLYMERIZATION CATALYST BY ABSTRACTION WITH LEWIS ACIDS

[75] Inventors: Robert E. LaPointe; James C. Stevens; Peter N. Nickias; Mark H. McAdon, all of Midland, Mich.

[73] Assignee: The Dow Chemical Company, Midland, Mich.

[21] Appl. No.: 876,268

[22] Filed: May 5, 1992

Related U.S. Application Data

[63] Continuation-in-part of Ser. No. 720,041, Jun. 24, 1991, abandoned.

[51] Int. Cl.$^6$ .................................................. B01J 31/00
[52] U.S. Cl. ..................... 502/117; 502/103; 502/152; 502/155; 526/170
[58] Field of Search .................................. 502/152, 155, 502/103, 104, 117

[56] References Cited

U.S. PATENT DOCUMENTS

| | | | |
|---|---|---|---|
| 5,026,798 | 6/1991 | Canich | 502/127 |
| 5,055,438 | 10/1991 | Canich | 502/117 |
| 5,064,802 | 11/1991 | Stevens et al. | 502/155 |

FOREIGN PATENT DOCUMENTS

| | | |
|---|---|---|
| 0427697 | 5/1991 | European Pat. Off. |

OTHER PUBLICATIONS

Zambelli et al, Macromolecules, 1989 (22), pp. 2186–2189 no month available.
JACS, 113, 3623–25 (1990) (no month available).
J. Org. Chem., 22, pp. 659–663 (1970) (no month available).
J. Am. Chem. Soc. 112, 8750–8754, Lazlo et al., 1990 no month available.
J. Poly. Sci. Poly. Chem. Ed. 12, 1799–1807, Furukawa et al., 1974 no month available.
Can. J. Chem. 60, 801–808 Childs et al., 1982 no month available.

*Primary Examiner*—Glenn Caldarola
*Assistant Examiner*—Elizabeth Wood

[57] ABSTRACT

A process for preparing addition polymerization catalysts having a limiting charge separated structure corresponding to the formula:

$$LMX^+XA^-,$$

wherein:

L is a derivative of a substituted delocalized π-bonded group imparting a constrained geometry to the metal active site and containing up to 50 nonhydrogen atoms;

M is a metal of Group 4 or the Lanthanide series of the Periodic Table of the Elements;

X independently each occurrence is hydride or a hydrocarbyl, silyl or germyl group having up to 20 carbon, silicon or germanium atoms; and $A^-$ is an anion of a Lewis acid, A, having relative Lewis acidity greater than or equal to that of phenylbis (perfluorophenyl)borane, said anion being compatible with the metal cation, the steps of the process comprising contacting a derivative of a Group 4 or Lanthanide metal corresponding to the formula:

$$i\, LMX_2,$$

wherein

L, M, and X are as previously defined, with the Lewis acid, A, under conditions to cause abstraction of X and formation of the anion $XA^-$.

10 Claims, No Drawings

HOMOGENEOUS OLEFIN POLYMERIZATION CATALYST BY ABSTRACTION WITH LEWIS ACIDS

CROSS-REFERENCE TO RELATED APPLICATION

This is a continuation-in-part of application Ser. No. 07720,041, filed Jun. 24, 1991 and now abandoned, the teachings of which are herein incorporated by reference thereto.

BACKGROUND OF THE INVENTION

This invention relates to a method for preparing compositions of matter that are useful as addition polymerization catalysts. More particularly, this invention relates to a method for preparing homogeneous, constrained geometry, cationic, catalyst compositions by abstraction with Lewis acids.

In U.S. Ser. No. 545,403, filed Jul. 3, 1990 there are disclosed and claimed certain constrained geometry metal complexes having utility as homogeneous olefin polymerization catalysts. In, U.S. Ser. No. 547,728, also filed Jul. 3, 1990 and now U.S. Pat. No. 5,064,802 cationic monocyclopentadienyl metal complexes with salts of Bronsted acids containing a non-coordinating compatible anion are disclosed and claimed. Finally, in U.S. Ser. No. 547,718, coincidentally also filed on Jul. 3, 1990 and now abandoned, an oxidative activation technique for preparing such cationic catalysts is disclosed and claimed. For the teachings contained therein the above mentioned pending U.S. applications are herein incorporated in their entirety by reference thereto.

In *J. Am. Chem. Soc.* 113, 3623–3625 (1991) there is disclosed a process for preparation of "cation like" zirconocene polymerization complexes by alkyl abstraction using tris(pentafluorophenyl)borane. The complexes were stated to have activity roughly comparable to typical complexes based on alumoxane. No suggestion as to the suitability of the disclosed technique for use with constrained geometry metal catalysts is provided by the reference.

In J. Organometal. Chem., 22, 659–663 (1970), there is disclosed the reaction between tetramethyltitanium and triphenylborane or tribenzylborane. The authors postulate the intermediate formation of cationic titanium species which were not isolated during the reaction. No suggestion as to the suitability of the disclosed reaction for use in catalysis is provided by the reference.

Previously known techniques for preparing cationic metal complexes having constrained geometry have been disadvantaged by requiring difficult synthetic procedures to prepare the necessary precursors and low yields of isolated products. It would be desirable if there were provided an improved technique for preparing cationic metal complexes having constrained geometry which avoids difficult synthetic procedures and poor yields.

It has now been discovered that the foregoing and other disadvantages of the prior art cationic, olefin polymerization catalysts can be avoided or at least reduced with the process of the present invention. Surprisingly the catalysts of the present invention are marked by extremely high catalytic effectiveness as measured by polymer yield at a given temperature.

SUMMARY OF THE INVENTION

In accordance with the present invention there is provided a process for preparing a catalyst having a limiting charge separated structure corresponding to the formula:

$$LMX^+XA^-,$$

wherein:

L is a derivative of a substituted delocalized π-bonded group imparting a constrained geometry to the metal active site and containing up to 50 nonhydrogen atoms;

M is a metal of Group 4 or the Lanthanide series of the Periodic Table of the Elements;

X independently each occurrence is hydride or a hydrocarbyl, silyl or germyl group having up to 20 carbon, silicon or germanium atoms; and A⁻ is an anion of a Lewis acid, A, having relative Lewis acidity greater than or equal to that of phenylbis (perfluorophenyl)borane, said anion being compatible with the metal cation, the steps of the process comprising contacting a derivative of a Group 4 or Lanthanide metal corresponding to the formula:

$$LMX_2,$$

wherein

L, M, and X are as previously defined, with the Lewis acid, A, under conditions to cause abstraction of X and formation of the anion XA⁻.

Preferably M is a metal of Group 4 of the Periodic Table of the Elements, most preferably titanium or zirconium. Also, preferably X is $C_1$–$C_{10}$ hydrocarbyl, most preferably methyl.

The preceding formula for the catalyst compositions is referred to as the limiting, charge separated structure. However, it is to be understood that, particularly in solid form, the catalyst may not be fully charge separated. That is, the X group may retain a partial covalent bond to the metal atom, M. Thus, the catalysts may be alternately depicted as an ion pair possessing the formula:

$$LMX..X..A.$$

The catalysts are preferably prepared by contacting the derivative of a Group 4 or Lanthanide metal with the Lewis Acid in an inert diluent such as an organic liquid.

Suitable anions are those that either do not coordinate to or are only weakly coordinated to said cation, thereby remaining sufficiently labile to be displaced by a neutral Lewis base. A "compatible" anion additionally refers to such an anion that, when functioning as a charge balancing anion in the catalyst system of this invention, within the time frame of the desired end use, does not transfer an anionic substituent or fragment thereof to the cation thereby forming a neutral metallocene and a neutral metal byproduct. In addition such anions are not degraded to neutrality when the initially formed complex decomposes and are noninterfering with desired subsequent polymerizations or other uses of the complex.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

By use of the term "constrained geometry" herein is meant that the metal atom is forced to greater exposure of the active metal site because one or more substituents on the substituted delocalized π-bonded group forms a portion of a ring structure including the metal atom, wherein the metal is both bonded to an adjacent covalent moiety and held in association with the substituted delocalized π-bonded group through an η⁵ or other π-bonding interaction. It is understood that each respective bond between the metal atom and the constituent atoms of the substituted delocalized π-bonded group need not be equivalent. That is, the metal may be symmetrically or unsymmetrically π-bound to the substituted delocalized π-bonded group.

The geometry of the active metal site is further defined as follows. The center of the substituted delocalized π-bonded group may be defined as the average of the respective X, Y, and Z coordinates of the atomic centers forming the substituted delocalized π-bonded group. The angle, Θ, formed at the metal center between the center of the ligating atom of each other ligand of the metal complex may be easily calculated by standard techniques of single crystal X-ray diffraction. Each of these angles may increase or decrease depending on the molecular structure of the constrained geometry metal complex. Those complexes wherein one or more of the angles, Θ, is less than in a similar, comparative complex differing only in the fact that the constrain-inducing substituent is replaced by hydrogen have constrained geometry for purposes of the present invention. Preferably one or more of the above angles, Θ, decrease by at least 5 percent, more preferably 7.5 percent, compared to the comparative complex. Highly preferably, the average value of all bond angles, Θ, is also less than in the comparative complex.

Preferably, metal coordination complexes of Group 4 or Lanthanide metals according to the present invention have constrained geometry such that the smallest angle, Θ, is less than 115°, more preferably less than 110°, most preferably less than 105°.

Substituted delocalized π-bonded groups for use herein include any π-electron containing moiety capable of forming a delocalized bond with the Group 4 or Lanthanide metal and further substituted with one or more divalent substituents that are also covalently bound to the metal. Divalent substituents preferably include groups containing up to 30 nonhydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M. Examples of suitable delocalized, π-bonded groups are cyclopentadienyl- or allyl-groups, and derivatives thereof.

Highly preferred Group 4 or Lanthanide metal derivatives are substituted monocyclopentadienyl compounds corresponding to the formula:

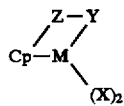  I wherein:

M is titanium or zirconium;

Cp is a cyclopentadienyl group or derivative thereof that is π-bound to M and substituted at least by Z;

Z is a divalent moiety comprising oxygen, sulfur, boron, or a member of Group 14 of the Periodic Table of the Elements;

Y is a ligand group comprising nitrogen, phosphorus, oxygen or sulfur or optionally Z and Y together form a fused ring system; and X is as previously defined.

After abstraction of the X group, the highly preferred catalysts of the invention have a limiting, electron separated structure corresponding to the formula:

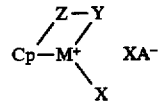  II wherein Cp, Z, M, X and A are as previously defined.

By the term "derivative" is meant that each atom in the delocalized π-bonded group may independently be substituted with a radical selected from the group consisting of hydrocarbyl radicals, substituted-hydrocarbyl radicals wherein one or more hydrogen atoms are replaced by a halogen atom, hydrocarbyl-substituted metalloid radicals wherein the metalloid is selected from Group 14 of the Periodic Table of the Elements, and halogen radicals. Suitable hydrocarbyl and substituted-hydrocarbyl radicals used to form derivatives of the delocalized π-bonded group will contain from 1 to 20 carbon atoms and include straight and branched alkyl radicals, cyclic hydrocarbon radicals, alkyl-substituted cyclic hydrocarbon radicals, aromatic radicals and alkyl-substituted aromatic radicals. In addition two or more such radicals may together form a fused ring system or a hydrogenated fused ring system. Examples of the latter are indenyl-, tetrahydroindenyl-, fluorenyl-, and octahydrofluorenyl- groups. Suitable hydrocarbyl-substituted organometalloid radicals include mono-, di- and trisubstituted organometalloid radicals of Group 14 elements wherein each of the hydrocarbyl groups contains from 1 to 20 carbon atoms. More particularly, suitable hydrocarbyl-substituted organometalloid radicals include trimethylsilyl, triethylsilyl, ethyldimethylsilyl, methyldiethylsilyl, triphenylgermyl, trimethylgermyl and the like.

Most highly preferred derivatives of Group 4 or Lanthanide metals are amidosilanediyl- or amidoalkanediyl-compounds corresponding to the formula:

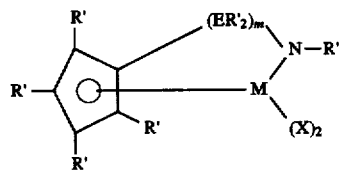

wherein:

M is titanium or zirconium, bound to an η⁵-cyclopentadienyl group;

R' each occurrence is independently selected from hydrogen, silyl, alkyl, aryl and combinations thereof having up to 20 carbon or silicon atoms, and optionally two or more R' groups on the cyclopentadienyl group may form a fused ring system;

E is silicon or carbon;

X independently each occurrence is hydride, alkyl, aryl or halogen substituted aryl of up to 20 carbons; and m is 1 or 2.

Examples of the above most highly preferred metal coordination compounds include compounds wherein the R' on the amido group is methyl, ethyl, propyl, butyl, pentyl, hexyl, (including branched and cyclic isomers), norbornyl, benzyl, phenyl, etc.; the cyclopentadienyl group is cyclopentadienyl, indenyl, tetrahydroindenyl, fluorenyl, tetrahydrofluorenyl, octahydrofluorenyl, etc.; R' on the foregoing cyclopentadienyl groups each occurrence is hydrogen, methyl, ethyl, propyl, butyl, pentyl, hexyl, (including branched and cyclic isomers), norbornyl, benzyl, phenyl, etc.; and X is methyl, neopentyl, trimethylsilyl, norbornyl, benzyl, methylbenzyl, phenyl, pentafluorophenyl, etc.

Illustrative derivatives of Group 4 or Lanthanide metals that may be employed in the practice of the present invention include: [dimethyl(tert-butylamido)(tetramethyl-$\eta^5$-cyclopentadienyl)silane]dibenzylzirconium, [dimethyl(tert-butylamido)(tetramethyl-$\eta^5$-cyclopentadienyl)silane] dibenzyltitanium, [dimethyl(tert-butylamido)(tetramethyl-$\eta^5$-cyclopentadienyl)silane]dimethyltitanium, [(tert-butylamido)(tetramethyl-$\eta^5$-cyclopentadienyl)-1,2-ethanediyl]dimethylzirconium, [(tert-butylamido)(tetramethyl-$\eta^5$-cyclopentadienyl)-1,2-ethanediyl] dibenzyltitanium, [(methylamido)($\eta^5$-cyclopentadienyl)-1,2-ethanediyl]dibenzhydrylzirconium, [(methylamido)(tetramethyl-$\eta^5$-cyclopentadienyl)-1,2-ethanediyl] dineopentyltitanium, [(phenylphosphido)(tetramethyl-$\eta^5$-cyclopentadienyl)methylene]diphenyltitanium, [dibenzyl (tert-butylamido)(tetramethyl-$\eta^5$-cyclopentadienyl)silane] dibenzylzirconium, [dimethyl(benzylamido)($\eta^5$-cyclopentadienyl)silane]di(trimethylsilyl)titanium, [dimethyl(phenylphosphido)(tetramethyl-$\eta^5$-cyclopentadienyl)silane]dibenzylzirconium, [dimethyl(tert-butylamido)(tetramethyl-$\eta^5$-cyclopentadienyl)silane] dibenzylhafnium, [(tetramethyl-$\eta^5$-cyclopentadienyl)-1,2-ethanediyl]dibenzyltitanium, [2-$\eta^5$-(tetramethylcyclopentadienyl)-1-methyl-ethanolato (2-)] dibenzyltitanium, [2-$\eta^5$-(tetramethylcyclopentadienyl)-1-methyl-ethanolato (2-)]dimethyltitanium, [2-$\eta^5$-(tetramethylcyclopentadienyl)-1-methyl-ethanolato (2-)] dibenzylzirconium, [2-$\eta^5$-(tetramethylcyclopentadienyl)-1-methyl-ethanolato (2-)]dimethylzirconium, [2-[(4a, 4b, 8a, 9, 9a -$\eta$)-9H-fluoren-9-yl]cyclohexanolato (2-)] dimethyltitanium, [2-[(4a, 4b, 8a, 9, 9a -$\eta$)-9H-fluoren-9-yl]cyclohexanolato (2-)]dibenzyltitanium, [2-[(4a, 4b, 8a, 9, 9a -$\eta$)-9H-fluoren-9-yl]cyclohexanolato (2-)] dimethylzirconium, [2-[(4a, 4b, 8a, 9, 9a -$\eta$)-9H-fluoren-9-yl]cyclohexanolato (2-)]dibenzylzirconium, and the like.

Other compounds which are useful in the catalyst compositions of this invention, especially compounds containing other Group 4 or Lanthanide metals, will, of course, be apparent to those skilled in the art.

In the most preferred embodiment —Z—Y— is an amidosilane or amidoalkane group of up to 10 nonhydrogen atoms, that is, (tert-butylamido)(dimethylsilyl), (tert-butylamido)-1-ethane-2-yl, etc.

The Lewis acids having Lewis acidity suitable for use according to the present invention are prepared according to known techniques such as those of Marks, et al. *J. Am. Chem. Soc.* 1991, 113, 3623–3625, or J. Pohlman, et al., *Naturforschg.* 1965, 20b, 5–11. The preferred technique is to combine a boron or aluminum halide compound such as boron trichloride or boron trifluoride with an alkali metal or alkaline earth derivative of the desired substituent or substituents. Additionally, borate esters such as tris (perfluorophenyl) borate may be prepared by the reaction of pentafluorophenylphenol and borane-methyl sulfide complex according to the method of *J. Org. Chem.*, 43(13) 2731-32 (1978).

Lewis acidity may be measured by empirical means and may also be predicted with a high degree of certainty based on theoretical methods. A preferred technique for measuring Lewis acidity is the proton NMR chemical shift of the proton on carbon #3 (H-3) of crotonaldehyde complexes of the Lewis acid. This technique was disclosed by R. Childs et al., Can. J. Chem., 1982, 802–808. A similar technique for determining Lewis acidity was taught in P. Laslo et al. J. Am. Chem. Soc. 1990, 12, 8750–8754. The units of measurement are $\Delta\delta$ (ppm). It has been discovered that the technique may be practiced at temperatures at or less than 25° C. without deleterious effect.

The difference in chemical shift of the 3-hydrogen of free, uncomplexed crotonaldehyde and the 3-hydrogen of the complexed Lewis acid adduct is determined. This chemical shift difference ($\Delta\delta$ in ppm) is related to the Lewis acidity of the species under study, with the trend being the more downfield the 3-hydrogen is shifted, the greater the Lewis acidity of the compound being examined. The chemical shift difference of phenylbis(perfluorophenyl)borane is 0.77 ppm. More Lewis acidic compounds have chemical shift differences, $\Delta\delta$, more than 0.77. Preferred Lewis acids have an acidity from 0.77 to 1.49, more preferably from 1.0 to 1.49. Thus, by the Childs et al. technique, useful Lewis acids for the present invention are acids having relative acidity compared to phenylbis(perfluorophenyl)borane, $\Delta\delta'-\Delta\delta°$, $\geq 0$ (where $\Delta\delta'$ is the Lewis acidity of the candidate Lewis acid and $\Delta\delta°$ is the Lewis acidity of phenylbis (perfluorophenyl)borane). Preferred Lewis acids are those having relative acidity from 0 to 0.72, more preferably from 0.23 to 0.72.

Detrimental reactivity of Lewis acids includes abstraction of one or more groups from the anion by the cationic portion of the catalyst, LMX+. Readily extractable groups comprise the halides when such halide is directly attached to a central Group 13 metalloid. Thus, most preferred non-reactive Lewis acids are Lewis acids that are devoid of halide groups directly attached to a central Group 13 metalloid, especially boron. Stated otherwise, most preferred Lewis acids are boron compounds devoid of halogen moieties directly attached to the boron.

Theoretical techniques may also be utilized to calculate the acidity of Lewis acids suitable for use according to the present invention. Several commercially available computer programs may be used to calculate the Lewis acidity. In a preferred technique theoretical structures and total energies may be calculated for candidate molecules in a proposed reaction of a Lewis acid with a Lewis base to form a complex. Molecules giving larger calculated heats of complexation indicate greater Lewis acidity. A program such as GAUSSIAN 90, or similar molecular simulation software may be used for the simulation and analysis of such materials.

First, the initial structures are optimized by minimizing the calculated total energy with respect to all degrees of freedom: bond lengths, bond angles, and torsional angles. The heat of reaction ($\Delta H$) is then calculated as being the difference between the total energy of the products and the total energy of the reactants e.g., $$\Sigma E_{(products)} - \Sigma E_{(reactants)},$$

where

E is approximated by the quantum mechanical energy ($E_{QM}$) at absolute zero temperature (0° Kelvin) for reactants and products.

By the foregoing technique the Lewis acidity of a compound towards a Lewis base such as methyl anion ($CH_3$—) or ammonia can be calculated, using the formula:

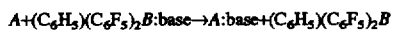

$$A + (C_6H_5)(C_6F_5)_2B:base \rightarrow A:base + (C_6H_5)(C_6F_5)_2B$$

where A is the Lewis acid and "base" is the Lewis base. If the reaction is exothermic ($\Delta H < 0$), then A is a stronger Lewis acid than phenylbis(perfluorophenyl)boron. Relative acidity is determined by comparison to the calculated $\Delta H$ of phenylbis(perfluorophenyl)boron, which by definition is 0.0 kcal/mole.

Based on the foregoing empirical and theoretical techniques highly preferred Lewis acids are: tris (pentafluorophenyl)borane, tris (2,3,5,6-tetrafluorophenyl) borane, tris(2,3,4,5-tetrafluorophenyl)borane, tris(3,4,5-trifluorophenyl)borane, tris(1,2,2-trifluoroethenyl)borane, phenylbis(perfluorophenyl)borane, tris(3,4,5-trifluorophenyl)aluminum, tris(perfluorophenyl) borate, 1,3, 5-cyclohexanetriol borate (cyclohexane-r-1, c-3, c-5-triol borate), and 1,1,1-trimethylolethane borate (2,6,7-trioxa-1-bora-4-methylbicyclo[2.2.2]octane) (the latter two compounds may be prepared according the technique of U.S. Pat. No. 2,909,560, by the condensation of 1,3,5-cyclohexanetriol or 1,1,1-trimethylolethane with boric acid).

Without wishing to be bound by any particular theory of operation it is believed that the Lewis acid causes the abstraction of the X group and in the process becomes an anionic species. This result is believed to be of practical significance for the present invention where the Lewis acid is a stronger Lewis acid than the resulting cation, LMX$^+$. The specific Lewis acids of the present invention are highly effective in this regard.

In general, the catalyst can be prepared by combining the two components (the derivative of a Group 4 or Lanthanide metal and the Lewis acid) in a suitable solvent at a temperature within the range from $-100°$ C. to $300°$ C., preferably $25°$ to $50°$ C. Suitable solvents include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, perfluorinated hydrocarbons such as perfluorinated $C_{4-10}$ alkanes and aromatic and alkyl-substituted aromatic compounds such as benzene, toluene and xylene. Suitable solvents also include liquid olefins which may act as monomers or comonomers including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene and vinyltoluene (including all isomers alone or in admixture). Preferred solvents are aliphatic hydrocarbons especially $C_5$–$C_{10}$ alkanes or cycloalkanes and mixtures thereof.

The catalyst may be used to polymerize addition polymerizable monomers having from 2 to 1000 carbon atoms. Examples include: ethylenically unsaturated compounds, acetylenic compounds, conjugated or nonconjugated dienes, polyenes, and carbon monoxide. Preferred addition polymerizable monomers are olefins or diolefins having from 2 to 18 carbon atoms. Examples include the $C_{2-18}$ $\alpha$-olefins especially ethylene, propylene, isobutylene, 1-butene, 1-hexene, 4-methyl-1-pentene, 1-octene, 1-nonene, 1-decene, 1-dodecene, 1-tetradecene, 1-hexadecene, and 1-octadecene. Other preferred monomers include styrene, halo- or alkyl substituted styrenes, tetrafluoroethylene, vinylbenzocyclobutane, 1,4-hexadiene, norbornene, and substituted norbornenes such as 5-ethylidene-2-norbornene. Most preferred monomers are $\alpha$-olefins having from 2 to 12 carbon atoms either alone or in combination. The catalyst may also be used to polymerize $\alpha$-olefins, diolefins and/or acetylenically unsaturated monomers in combination with other unsaturated monomers.

In general, the polymerization may be accomplished at conditions well known in the prior art for Ziegler-Natta or Kaminsky-Sinn type polymerization reactions, that is, temperatures from $0°$ to $250°$ C. and pressures from atmospheric to 1000 atmospheres (100 MPa). Suspension, solution, slurry or other process condition may be employed if desired. A support may be employed but preferably the catalysts are used in a homogeneous manner. It will, of course, be appreciated that the catalyst system will form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization mixture.

It is believed that the active catalyst species of the present invention contains a metal center which center remains cationic, unsaturated and has a metal-carbon bond which is reactive with olefins, diolefins and acetylenically unsaturated compounds. Also associated with this metal center is a charge balancing anionic remnant of the formula $XA^{3^1}$. As previously mentioned the catalyst may also exist in a less than fully charge-separated configuration.

The catalyst formed by the method of this invention may be retained in solution or separated from the solvent, isolated, and stored for subsequent use. As previously indicated supra, the catalyst may also be prepared in situ during a polymerization reaction by passing the separate components into the polymerization vessel where the components will contact and react to produce the catalyst.

The equivalent ratio of derivative of a Group 4, or Lanthanide metal compound to Lewis acid employed is preferably in a range (complex: Lewis acid) from 0.1:1 to 10:1, more preferably from 0.2:1 to 5:1, most preferably 0.5:1.0 to 1:2. In most polymerization reactions the equivalent ratio of catalyst:polymerizable compound employed is from $10^{-12}:1$ to $10^{-1}:1$, more preferably from $10^{-9}:1$ to $10^{-4}:1$.

A beneficial feature of the catalysts of this invention, especially the titanium based catalysts, is that when the catalysts of this invention are used to copolymerize olefins, either alone or in combination with diolefins, the amount of higher molecular weight olefin or diolefin incorporated into the copolymer is significantly increased when compared to copolymers prepared with the more conventional Ziegler-Natta type catalysts. In addition, when compared to constrained geometry catalysts containing alumoxane, the catalysts of the present invention possess higher activities. Typically, catalyst efficiencies of the present catalysts (measured by weight of polymer produced/catalyst weight) are at least five times greater than that obtained with comparable alumoxane containing catalysts.

In general, catalysts can be selected so as to produce polymer products which will be relatively free of large amounts of certain trace impurities such as aluminum, magnesium and chloride generally found in polymers produced with Ziegler-Natta type catalysts. The polymer products produced with the catalysts of this invention have a broader range of applications than polymers produced with more conventional Ziegler-Natta type catalysts comprising a halogenated metal alkyl such as magnesium chloride, or an alkyl aluminum chloride.

Having described the invention the following examples are provided as further illustration thereof and are not to be construed as limiting. Unless stated to the contrary all parts and percentages are expressed on a weight basis.

General Polymerization Procedure

Ethylene, propylene, and hydrogen were purified by passing through columns of 13× molecular sieve, activated alumina, and trace oxygen removal catalyst (alumina supported copper/manganese catalyst available from Englhardt Inc. under the tradename Q-5). Solvents and octene were degassed with nitrogen, then were purified by passing through columns of 13× molecular sieve, activated alumina, and trace oxygen removal catalyst. Phenylacetylene-free styrene was degassed with nitrogen, then purified by passing through a column of activated alumina. A 2 L stirred autoclave was charged with the desired amounts of a solvent and comonomer.

Hydrogen was added by differential pressure expansion from a 75 mL addition tank. The hydrogen pressure differential represents the difference in pressure between the starting and final pressure in the hydrogen addition tank after adding hydrogen to the 2 L reactor containing solvent and comonomer. The reactor was heated to the polymerization temperature and was saturated with ethylene to the desired pressure. Metal complex and Lewis acid cocatalyst were mixed in a drybox by syringing the desired amount of 0.0050M metal complex solution (in mixed alkane solvent (Isopar E™ available from Exxon Chemicals Inc.) or toluene) into a solution of the cocatalyst (in Isopar® E or toluene solvent). Optionally, additional solvent was added to facilitate transfer of the catalyst solution to the reactor. This solution was then transferred to a catalyst addition tank and injected into the reactor.

The polymerization was allowed to proceed for the desired time and then the solution was drained from the bottom of the reactor and quenched with isopropanol. A hindered phenolic antioxidant (Irganox® 1010, available from Ciba-Geigy Corporation) was added and the polymer was air dried overnight. The residual solvent was removed in a vacuum oven overnight.

Polymer melt indices (I2) were measured according to ASTM D-1238, Procedure A, Condition E, using a micro-melt indexer, Model CS-127MF, available from Custom Scientific Instruments, Inc. Densities are determined by buoyancy measurements of compression molded samples in methyl ethyl ketone.

Experimental Determination of Lewis acidity

The Lewis acidity of phenylbis(perfluorophenyl)borane was determined using NMR analysis substantially according to the technique of R. Childs, et al., Can. J. Chem., 1982, 60, 802–808. All manipulations were carried out either using standard Schlenk and/or high vacuum techniques or in an inert glovebox (Vacuum Atmospheres, Inc.) under recirculating, dry nitrogen with oxygen levels in the glove box being continuously monitored with an oxygen analyzer and maintained at <1 ppm. Crotonaldehyde purified by vacuum-transfer from calcium hydride and methylene chloride-$d_2$ ($CD_2Cl_2$) vacuum transferred from phosphorus pentoxide were used.

Proton NMR spectra were recorded either on a Varian VXR-300 NMR spectrometer or a Varian Gemini 300 NMR spectrometer. Chemical shifts were determined relative to tetramethylsilane through the residual $CHDCl_2$ ($^1H$, $\delta5.32$) in $CD_2Cl_2$. The NMR samples were prepared by adding an appropriate quantity of the Lewis acid compound to a solution of crotonaldehyde in $CD_2Cl_2$ at $-20°$ C. and allowing the sample to warm slowly to room temperature. The stoichiometry of the resulting solution was such that there was a 50 percent excess of the Lewis acid reagent with a total concentration of reactants being about 0.3M. The $^1H$ NMR spectrum was then recorded, and H-3 NMR shift of the Lewis acid adduct of crotonaldehyde and free crotonaldehyde determined.

Theoretical calculation of Lewis acidity

Structures and energies were calculated using one or more of the following standard techniques of electronic structure theory.

1. AM1—Dewar's semi-empirical method based on approximate molecular orbital theory. AM1 has been parametrized to fit selected experimental data. AM1 calculation techniques are well known to those skilled in the art, and are described in, for example, M. J. S. Dewar, E. G. Zoebisch, E. F. Healy, and J. J. P. Stewart, *J. Am. Chem. Soc.*, 107, 3902 (1985); M. J. S. Dewar and Eve G. Zoebisch, *J. Mol. Struct. (THEOCHEM)* 180, 1 (1988); M. J. S. Dewar, C. Jie, and E. G. Zoebisch, *Organometallics*, 7, 513 (1988); M. J. S. Dewar and C. Jie, *Organometallics*, 6, 1486 (1987); M. J. S. Dewar and K. M. Merz, Jr., *Organometallics* 7, 522–4 (1988); M. J. S. Dewar and C. Jie, *Organometallics*, 8, 1547 (1989); M. J. S. Dewar and C. Jie, *Organometallics*, 8, 1544–7 (1989); and M. J. S. Dewar and A. J. Holder, *Organometallics*, 9, 508 (1990).

The AM1 calculations are performed with the program MOPAC, version 5.00, available from the Quantum Chemistry Program Exchange (QCPE), Department of Chemistry, Indiana University, Bloomington, Ind. 47405. The program is further described in the MOPAC Manual, J. J. P. Stewart, Frank J. Seiler, Res. Lab., U.S. Air Force Academy, Colo. Spgs., Conn. 80840

2. HF (restricted Hartree-Fock) the rigorous (abinitio, no adjustable parameters) method. The HF results were calculated using the GAUSSIAN® 90 program and the well-known 3–21 g basis set. The 3–21 g basis set is a valence double-zeta basis set. Gaussian 90, Revision J, available from Gaussian, Inc., Pittsburgh Pa., 1990.

The 3–21 G basis set is well known in the art, and is described in, for example, W. J. Hehre, L. Radom, P. v. R. Schleyer, and J. A. Pople, *Ab Initio Molecular Orbital Theory*, Wiley, New York, (1986); Pietro, W. J., et al., *J. Am. Chem. Soc.* 104, 5039–48 (1982); M. S. Gordon, et al, *J. Am. Chem. Soc.* 104, 2797–803 (1982); J. S. Binkley, et al., *J. Am. Chem. Soc.* 102, 939–47 (1980); K. D. Dobbs and W. J. Hehre, *J. Comput. Chem.* 8, 880–93 (1987); K. D. Dobbs and W. J. Hehre, *J. Comput. Chem.* 8, 861 (1987); K. D. Dobbs and W. J. Hehre, *J. Comput. Chem.* 9, 801 (1988); K. D. Dobbs and W. J. Hehre, *J. Comput. Chem.* 7, 359 (1986).

EXAMPLE 1

A catalyst solution was prepared by combining 1 mL of a 0.005M toluene solution of tris(pentafluorophenyl)borane with 1 mL of a 0.005M toluene solution of [(tert-butylamido)dimethyl(tetramethyl-$\eta^5$-cyclopentadienyl) silane dibenzyl titanium [[($C_5Me_4$)$SiMe_2$N(t-Bu)]Tibz$_2$] (prepared by reaction of (tert-butylamido)dimethyl (tetramethyl)-$\eta^5$-cyclopentadienyl)silane titanium dichloride and benzyl lithium. The dichloride in turn was prepared by reaction of lithium 1,2,3,4-tetramethylcyclopentadienide with (N-t-butylamino)(dimethyl)silane chloride, followed by conversion to the dilithium salt, reaction with $TiCl_3$ to form the closed ring structure (N-t-butylamido)dimethyl (tetramethyl-$\eta^5$-cyclopentadienyl)titanium chloride, and oxidation of the metal center with methylene chloride to form (N-t-butylamido)dimethyl(tetramethyl-$\eta^5$-cyclopentadienyl)titanium dichloride. The mixture was shaken for 10 seconds at 25° C., giving a catalyst solution noticeably darker than the starting, red-orange, titanium containing solution.

Polymerization

The catalyst solution was combined with a mixture comprising 1 L of Isopar E™, 0.2 L of 1-octene, and ethylene (31 atmospheres, 3.1 MPa) in a 2 L reactor. The reactants were previously deaerated and purified and the reactor contents were heated to 130° C. An immediate 7° C. rise in reactor temperature occurred. Ethylene was provided on demand at 3.1 MPa. After 10 minutes the reactor contents were removed and devolatilized giving 80.0 g of ethylene-octene copolymer having a micro-melt index of 0.104.

EXAMPLE 2

A catalyst solution was prepared by combining 1 mL of a 0.005M toluene solution of tris(pentafluorophenyl)borane with 1 mL of a 0.005M toluene solution of (tert-butylamido) dimethyl(tetramethyl-$\eta^5$-cyclopentadienyl)silane dibenzyl zirconium [($C_5Me_4$)$SiMe_2$N(t-Bu)]$Zrbz_2$] (prepared according to the same technique as Example 1). The mixture was shaken for 10 seconds at 25° C., giving a catalyst solution slightly darker than the starting, light yellow, zirconium containing solution.

Polymerization

The catalyst solution (10 μmol in 2 ml Isopar™ E) was combined with a mixture comprising 0.8 L of Isopar E™ and 0.4 liters of propylene in a 2 L reactor. The reactor contents were heated to 50° C. After 45 minutes the reactor contents were removed and devolatilized giving 30.1 g of polypropylene having a micro-melt index of 24.3 and a syndiotactic index (measured at a racemic triad) of 83.5.

EXAMPLES 3–37

The metal complex for Examples 3–37 was (tert-butylamido)dimethyl(tetramethyl-5-cyclopentadienyl)silane titanium dimethyl, [($C_5Me_4$)$SiMe_2$N(t-Bu)]$TiMe_2$, and the Lewis acid was tris(perfluorophenyl)borane, $B(C_6F_5)_3$. The polymerization time for all examples was 10 minutes. The results for Examples 3–37 are shown in Table I.

EXAMPLES 38–57

The catalyst and procedure of Examples 3–37 were used except that 1000 mL of Isopar® E was added to the reactor followed by various amounts of propylene. The desired amount of hydrogen was then added and the solution was heated to the reaction temperature. The solution was then saturated with ethylene at 475 psig (3.38 MPa). Equimolar amounts of the metal complex, [($C_5Me_4$)$SiMe_2$N(t-Bu)]$TiMe_2$ and the Lewis acid, $B(C_6F_5)_3$ were mixed in 2 mL of Isopar® E and this solution was transferred into the reactor to begin the polymerization. The reaction was allowed to proceed for 15 minutes with ethylene being supplied on demand at 475 psig (3.38 MPa). The propylene content of the polymer was determined by carbon NMR spectroscopy using the method of J. C. Randall, *Rev. Macromo. Chem. Phys.*, 29(2&3), 201–317, (1989). The results are shown in Table II.

TABLE I

| Ex | T (°C.) | $H_2$ ΔkPa | $C_2H_4$ MPa | 1-octene (mL) | Lewis acid (μMole) | Ti (μMoles) | Yield, g | MI (I2) | Density, g/mL |
|---|---|---|---|---|---|---|---|---|---|
| 3 | 204 | 300 | 3.45 | 0 | 15 | 10.00 | 15.1 | 37.9 | — |
| 4 | 190 | 340 | 3.45 | 0 | 9 | 6.00 | 18.7 | 27.54 | — |
| 5 | 190 | 0 | 3.45 | 0 | 9 | 6.00 | 6.3 | 0.04 | — |
| 6 | 190 | 170 | 3.45 | 0 | 9 | 6.00 | 25.8 | 5.5 | — |
| 7 | 176 | 300 | 3.45 | 0 | 6 | 4.00 | 30.2 | 10.6 | — |
| 8 | 210 | 170 | 3.45 | 0 | 15 | 10.00 | 8.6 | 21.23 | — |
| 9 | 190 | 170 | 3.45 | 0 | 9 | 6.00 | 14 | 5.23 | — |
| 10 | 204 | 50 | 3.45 | 0 | 15 | 10.00 | 7.1 | 1.6 | — |
| 11 | 170 | 170 | 3.45 | 0 | 6 | 4.00 | 40.6 | 1.99 | — |
| 12 | 190 | 170 | 3.45 | 0 | 9 | 6.00 | 17.1 | 3.54 | — |
| 13 | 190 | 170 | 3.45 | 0 | 9 | 6.00 | 16.7 | 5.34 | — |
| 14 | 176 | 50 | 3.45 | 0 | 6 | 4.00 | 26.2 | 0.2 | — |
| 15 | 190 | 170 | 3.45 | 0 | 9 | 6.00 | 20.4 | 4.34 | — |
| 16 | 170 | 0 | 3.45 | 0 | 6 | 4.00 | 28 | 0.04 | — |
| 17 | 210 | 0 | 3.45 | 0 | 15 | 10.00 | 1.1 | — | — |
| 18 | 163 | 340 | 3.28 | 55 | 1.25 | 1.25 | 22.4 | 3.54 | 0.9220 |
| 19 | 163 | 170 | 3.28 | 55 | 1.25 | 1.25 | 45.5 | 1.04 | 0.9173 |
| 20 | 150 | 170 | 3.28 | 55 | 1.25 | 1.25 | 77.3 | 1.35 | 0.9115 |
| 21 | 163 | 170 | 3.28 | 55 | 1.25 | 1.25 | 49.1 | 1.07 | 0.9189 |
| 22 | 170 | 280 | 3.28 | 28 | 1.25 | 1.25 | 30.1 | 1.93 | 0.9310 |
| 23 | 163 | 170 | 3.28 | 100 | 1.25 | 1.25 | 43.2 | 5.6 | 0.9077 |
| 24 | 163 | 170 | 3.28 | 55 | 1.25 | 1.25 | 10.2 | 0.76 | 0.9079 |
| 25 | 155 | 69 | 3.28 | 28 | 1.25 | 1.25 | 35.5 | 0.07 | 0.9190 |
| 26 | 163 | 170 | 3.28 | 55 | 1.25 | 1.25 | 39.7 | 1.44 | 0.9173 |
| 27 | 170 | 69 | 3.28 | 82 | 1.25 | 1.25 | 23.7 | 2.04 | 0.9125 |
| 28 | 170 | * | 3.28 | 28 | 1.25 | 1.25 | 22.9 | 0.19 | 0.9223 |
| 29 | 155 | 280 | 3.28 | 82 | 1.25 | 1.25 | 44 | 4.24 | 0.9116 |
| 30 | 163 | 170 | 3.28 | 10 | 1.25 | 1.25 | 16.1 | 0.15 | 0.9337 |
| 31 | 163 | 0 | 3.28 | 55 | 1.25 | 1.25 | 10.2 | 0.58 | 0.9154 |
| 32 | 163 | 170 | 3.28 | 55 | 1.25 | 1.25 | 30.8 | 1.14 | 0.9192 |
| 33 | 170 | 280 | 3.28 | 82 | 1.25 | 1.25 | 22.6 | 9.95 | 0.9206 |
| 34 | 155 | 69 | 3.28 | 82 | 1.25 | 1.25 | 42 | 1.01 | 0.9096 |
| 35 | 175 | 170 | 3.28 | 55 | 1.25 | 1.25 | 17.7 | 3.78 | 0.9214 |
| 36 | 163 | 170 | 3.28 | 55 | 1.25 | 1.25 | 32.1 | 0.81 | 0.9176 |
| 37 | 155 | 280 | 3.28 | 28 | 1.25 | 1.25 | 31.3 | 0.36 | 0.9266 |

TABLE II

| Ex | Propene (g) | Temp (°C.) | H₂ ΔkPa | Ti (μmol) | Yield, g | Melt Index (I2) | Propylene Mol % | Density, (g/mL) |
|---|---|---|---|---|---|---|---|---|
| 38 | 100 | 95 | 690 | .500 | 70.9 | 3.551 | 30.7 | 0.8520 |
| 39 | 86 | 550 | 550 | .375 | 109.0 | 0.671 | 40.0 | 0.8513 |
| 40 | 130 | 86 | 140 | .325 | 98.1 | 0.184 | 41.2 | 0.8522 |
| 41 | 100 | 95 | 0 | .325 | 71.7 | 0.063 | 31.9 | 0.8516 |
| 42 | 130 | 104 | 550 | .750 | 99.5 | 6.984 | 50.2 | 0.8514 |
| 43 | 100 | 95 | 340 | .375 | 92.8 | 0.956 | 46.0 | 0.8518 |
| 44 | 100 | 95 | 340 | .375 | 88.7 | 0.777 | 38.0 | 0.8516 |
| 45 | 50 | 95 | 340 | .375 | 79.1 | 0.372 | 24.2 | 0.8631 |
| 46 | 70 | 86 | 550 | .375 | 94.7 | 1.098 | 30.0 | 0.8544 |
| 47 | 100 | 80 | 340 | .300 | 96.8 | 0.261 | 34.3 | 0.8518 |
| 48 | 70 | 104 | 550 | .500 | 75.6 | 2.122 | 30.0 | 0.8540 |
| 49 | 100 | 110 | 340 | .750 | 91.6 | 4.093 | 38.2 | 0.8536 |
| 50 | 100 | 95 | 340 | .500 | 96.5 | 1.203 | 38.1 | 0.8501 |
| 51 | 70 | 86 | 140 | .250 | 72.8 | 0.000 | 28.2 | 0.8559 |
| 52 | 100 | 95 | 340 | .325 | 79.2 | 0.796 | 35.8 | 0.8491 |
| 53 | 100 | 95 | 340 | .325 | 82.3 | 0.674 | 37.5 | 0.8518 |
| 54 | 70 | 104 | 140 | .750 | 92.6 | 0.830 | 32.9 | 0.8533 |
| 55 | 100 | 95 | 340 | .325 | 82.5 | 0.733 | 35.2 | 0.8517 |
| 56 | 130 | 104 | 140 | .500 | 84.1 | 1.697 | 43.2 | 0.8497 |
| 57 | 100 | 95 | 340 | .325 | 83.1 | 0.503 | 36.8 | 0.8508 |

EXAMPLES 59-77

The procedure of Examples 3–37 was followed except that various amounts of styrene were added to the reactor followed by Isopar® E to make 1000 mL of total liquid volume. Various amounts of propylene were then added. The solution was heated to the reaction temperature. The solution is then saturated with ethylene at 480 psig (3.41 MPa). Equimolar amounts of the metal complex, [(C₅Me₄)SiMe₂N(t-Bu)]TiMe₂, and the Lewis acid, B(C₆F₅)₃ were mixed in 2 mL of Isopar® E and this solution was transferred into the reactor to begin the polymerization. The reaction was allowed to proceed for 10 minutes with ethylene being supplied on demand at 480 psig (3.41 MPa). The results are shown in Table III. Where provided, propylene and styrene contents were determined by carbon 13 NMR spectroscopy.

TABLE III

| Ex | Propylene (g) | Styrene (mL) | Temp (°C.) | Ti (μmol) | Yield, g | Melt Index (I2) |
|---|---|---|---|---|---|---|
| 58 | 70 | 121 | 82 | 1.25 | 57.3 | 0.078 |
| 59 | 100 | 225 | 100 | 1.25 | 34.3 | 0.819 |
| 60 | 70 | 329 | 118 | 3.75 | 31.4 | 7.494 |
| 61 | 130 | 121 | 118 | 2.50 | 40.6 | 37.200 |
| 62* | 100 | 400 | 100 | 3.75 | 51.2 | 2.557 |
| 63 | 130 | 329 | 118 | 3.75 | 38.2 | 29.000 |
| 64 | 100 | 225 | 100 | 1.25 | 40.6 | 0.893 |
| 65 | 130 | 329 | 82 | 1.25 | 73.4 | 0.214 |
| 66 | 100 | 50 | 100 | 1.25 | 71.2 | 2.607 |
| 67 | 70 | 121 | 118 | 2.50 | 42.2 | 7.415 |
| 68 | 150 | 225 | 100 | 1.50 | 53.7 | 2.784 |
| 69 | 100 | 225 | 100 | 1.25 | 40.2 | 0.996 |
| 70 | 100 | 225 | 100 | 1.25 | 46.6 | 0.982 |
| 71 | 50 | 225 | 100 | 1.50 | 44.8 | 0.566 |
| 72 | 100 | 225 | 130 | 3.75 | 27.3 | 99.100 |
| 73 | 100 | 225 | 100 | 1.25 | 51.6 | 1.221 |
| 74 | 100 | 225 | 100 | 1.25 | 45.1 | 0.920 |
| 75 | 70 | 329 | 82 | 1.25 | 53.8 | 0.125 |
| 76 | 100 | 225 | 70 | 0.75 | 64.9 | 0.048 |
| 77 | 130 | 121 | 82 | 0.75 | 79.1 | 0.210 |

*Propylene 30 mole percent, styrene 4.4 mole percent

EXAMPLES 78-100

The procedure of Examples 3–37 was followed except that various amounts of styrene were added to the reactor followed by Isopar® E to make 1000 mL of total liquid volume. Various amounts of hydrogen were then added. The solution was heated to the reaction temperature. The solution was then saturated with ethylene at 475 psig (3.38 MPa). Equimolar amounts of the metal complex, [(C₅Me₄)SiMe₂N(t-Bu)]TiMe₂ and the Lewis acid, B(C₆F₅)₃ were mixed in 2 mL of Isopar® E and this solution was transferred into the reactor to begin the polymerization. Two additional charges of complex and Lewis acid were added at 5–10 minute intervals. The total amount of catalyst added (based on titanium) is shown in Table IV. The reaction was allowed to proceed for 10 minutes after the final catalyst addition with ethylene being supplied on demand at 475 psig (3.38 MPa) throughout the run. The results are shown in Table IV.

TABLE IV

| Ex | Styrene (mL) | Temp (°C.) | Hydrogen (kPa) | Catalyst (μmol) | Yield, g | Melt Index (I2) | Styrene Content (mole %) |
|---|---|---|---|---|---|---|---|
| 78 | 125 | 145 | 0 | 5.0 | 24.0 | 0.209 | 0.8 |
| 79 | 75 | 145 | 76 | 5.0 | 44.8 | 0.436 | 0.5 |
| 80 | 225 | 145 | 76 | 7.5 | 37.5 | 2.117 | 1.5 |
| 81 | 234 | 136 | 110 | 7.5 | 59.8 | 1.884 | 1.7 |
| 82 | 175 | 145 | 69 | 7.5 | 52.5 | 1.471 | 1.3 |

TABLE IV-continued

| Ex | Styrene (mL) | Temp (°C.) | Hydrogen (kPa) | Catalyst (μmol) | Yield, g | Melt Index (I2) | Styrene Content (mole %) |
|---|---|---|---|---|---|---|---|
| 83 | 175 | 145 | " | 7.5 | 52.0 | 1.352 | 1.4 |
| 84 | 234 | 154 | 28 | 7.5 | 34.4 | 2.447 | 1.5 |
| 85 | 116 | 136 | 110 | 5.8 | 65.1 | 0.739 | — |
| 86 | 275 | 145 | 69 | 7.5 | 46.2 | 2.055 | 1.9 |
| 87 | 175 | 160 | " | 7.5 | 31.1 | 7.111 | 1.2 |
| 88 | 175 | 130 | " | 3.0 | 46.3 | 0.335 | — |
| 89 | 116 | 154 | " | 7.5 | 49.2 | 4.061 | 1.0 |
| 90 | 234 | 154 | " | 7.5 | 39.8 | 9.417 | 1.6 |
| 91 | 175 | 145 | 140 | 7.5 | 55.1 | 3.494 | — |
| 92 | 175 | 145 | 69 | 7.5 | 53.1 | 1.144 | — |
| 93 | 116 | 154 | 28 | 7.5 | 46.4 | 0.710 | 0.8 |
| 94 | 175 | 145 | 69 | 7.5 | 52.6 | 1.134 | 1.4 |
| 95 | 234 | 136 | 28 | 5.0 | 45.5 | 0.270 | — |
| 96 | 175 | 145 | 69 | 7.5 | 52.2 | 1.185 | — |
| 97 | 175 | 145 | 0 | 7.5 | 50.2 | 0.465 | — |
| 98 | 175 | 145 | 69 | 7.5 | 51.3 | 1.126 | — |
| 99 | 75 | 145 | " | 7.5 | 63.0 | 0.489 | 0.6 |
| 100 | 116 | 136 | 28 | 5.0 | 52.5 | 0.115 | — |

EXAMPLE 101

The polymerization procedure of Examples 3–37 was followed using 1.25 micromoles of (tert-butylamido) dimethyl(tetramethyl-$\eta^5$-cyclopentadienyl)silane titanium dibenzyl [($C_5Me_4$)SiMe$_2$N(t-Bu)]Ti bz$_2$ and 1.25 micromoles of the Lewis acid, B($C_6F_5$)$_3$ mixed in 2 mL of Isopar® E. The reaction temperature was 160° C. 10 g of propylene and 100 Δpsi (0.7 MPa) hydrogen were added. The ethylene pressure was 460 psig (3.3 MPa). The polymerization time was 15 minutes. 22.9 g of an ethylene/propylene copolymer were isolated.

EXAMPLE 102

The polymerization procedure of Example 101 was followed using 1.00 micromoles of [($C_5Me_4$)SiMe$_2$N(t-Bu)]Ti (Me)$_2$ and 1.00 micromoles of the Lewis acid B($C_6F_5$)$_3$ mixed in 2 mL of Isopar® E. The reaction temperature was 90° C. 1000 mL of Isopar® E and 200 mL of 1-octene were charged into the reactor and no hydrogen was added. The ethylene pressure was 500 psig (3.55 MPa). The polymerization time was 15 minutes. 85.9 g of an ethylene/octene copolymer of approximately 0.87 g/mL density and melt index (I$_2$) of 0.3 was isolated.

EXAMPLE 103

Polymerization using (tert-butylamido)dimethyl (tetrahydrofluorene)silane titanium dimethyl metal derivative Preparation of tetrahydrofluorene 15 g (90.2 mmol) of fluorene was dissolved in 200 ml of a tetrahydrofuran (THF)/ethylene diamine solution (1:1 ratio). The solution was cooled in a ice bath and with stirring 3.13 g of lithium (451.2 mmol) was added in small portions. After all the lithium had been added the solution was stirred for 2 h with consequent dissolution of the lithium metal. The resulting solution was then poured into a HCl/ice mixture. The solution was then extracted with diethyl ether. The organic washings were combined, washed with water and dried over MgSO$_4$. The solution was filtered and the solvent removed on a rotary evaporator. The crude material was then purified by dissolving in hexane and passing through a silica gel column to give 11.4 g (75 percent yield) of product after solvent removal.

Preparation of lithium tetrahydrofluorenide 10 g of tetrahydrofluorene (59 mmol) was dissolved in 75 ml of pentane. To this solution 21 ml of n-butyl lithium (n-BuLi) (2.65M) was added dropwise over a 20 min period. The solution was stirred overnight with deposition of a white solid. The solid was collected by filtration, washed with pentane and dried under reduced pressure to give 7.14 g (70 percent yield) of product.

Preparation of (N-t-butylamino)(dimethyl) (tetrahydrofluorenyl)silane 5.78 g (34.9 mmol) of ClSiMe$_2$NHCMe$_3$ (prepared according to the method described in J. Prakt. Chem, 24(3–4), 226–30 (1964)) was added to 100 ml of THF. To this solution 6.15 g (34.9 mmol) of lithium tetrahydrofluorenide was added. The solution was then brought to reflux for 10 min and the solution cooled to room temperature. Gas chromatographic (GC) analysis showed the reaction to be complete. The solvent was then removed under reduced pressure, the residue extracted with pentane, filtered and the solvent again removed under reduced pressure to give 9.80 g of product (94 percent yield).

Preparation of dilithium (N-t-butylamido)(dimethyl) (tetrahydrofluorenyl)silane 9.80 g (32.8 mmol) of (N-t-butylamino)(dimethyl) (tetrahydrofluorenyl)silane was dissolved in 100 ml of diethylether. To this solution 26.6 ml (70.6 mmol) of nBuLi (2.65M) was added dropwise. Upon complete addition of the nBuLi the solution was stirred for 2 h whereupon the solvent was removed under reduced pressure to give an oily orange residue which solidified upon trituration with pentane to give 11.86 g (98 percent yield) of a yellow solid which was identified by nuclear magnetic resonance spectroscopy (NMR) as an etherate adduct (3/4 Et$_2$O per molecule) of dilithium (N-t-butylamino)(dimethyl)(tetrahydrofluorenyl) silane.

Preparation of [(N-t-butylamido)(dimethyl) (tetrahydrofluorenyl)silane]titanium dichloride ([(tetrahydrofluorenyl)SiMe$_2$N(t-Bu)]TiCl$_2$)

6 g (16.1 mmol) of TiCL$_3$(THF)$_3$ was dissolved in 75 ml of THF. To this solution 5.92 g (16.1 mmol) of dilithium (N-t-butylamido)(dimethyl)(tetrahydrofluorenyl)silane(3/4 Et$_2$O) was added as a solid with stirring. The solution was then stirred for 45 min, after this time period PbCl$_2$ (2.25 g, 8.1 mmol) was added and the solution stirred for 45 minutes. The THF was then removed under reduced pressure. The residue was then extracted with toluene, the solution filtered and the toluene removed under reduced pressure. The residue was then triturated with pentane and the solution cooled to −20° C. for 3 hours. The red precipitate was collected via filtration and washed with cold pentane and dried under vacuum to yield 5.00 g (75 percent yield) of product.

Preparation of [(N-t-butylamido)(dimethyl) (tetrahydrofluorenyl)silane]titanium dimethyl ([(tetrahydrofluorenyl)SiMe$_2$N(t-Bu)]Ti(CH$_3$)$_2$)

5.0 g of [(N-t-butylamido)(dimethyl) (tetrahydrofluorenyl)silane]titanium dichloride (12 mmol) was suspended in 100 ml of Et$_2$O. To this suspension 8.40 ml of methyl magnesium iodide (MeMgI) (3.0M in diethyl ether, Et$_2$O) was added dropwise with stirring over a 20 min period. Upon completion of the addition of the MeMgI the solution was stirred for 40 minutes. After this time period the Et$_2$O was removed under reduced pressure and the residue extracted with pentane, the solution filtered and the filtrate evaporated to dryness under reduced pressure to give 3.48 g (77 percent yield) of product.

Polymerization

The polymerization procedure of Example 102 was followed using 2.00 micromoles of [(tetrahydrofluorenyl) SiMe$_2$N(t-Bu)]Ti(CH$_3$)$_2$ and 2.00 micromoles of the Lewis acid, B(C$_6$F$_5$)$_3$ mixed in 2 mL of Isopar® E. The reaction temperature was 130° C. 808 g of Isopar® E and 100 g of 1-octene are charged into the reactor. No hydrogen was added. The ethylene pressure was 500 psig (3.55 MPa). The polymerization time was 15 minutes. 41.1 g of an ethylene/octene copolymer were isolated.

EXAMPLE 104

The procedure of example 103 was followed except that 2.50 micromoles of [(tetrahydrofluorenyl)SiMe$_2$N(t-Bu)]Ti (CH$_3$)$_2$ and 2.50 micromoles of the Lewis acid B(C$_6$F$_5$)$_3$, were mixed in 2 mL of Isopar® E were used to form the catalyst. The reaction temperature was 150° C. 829 g of Isopar® E and 29 g of 1-octene are charged into the reactor and no hydrogen was added. The ethylene pressure was 500 psig (3.55 MPa). The polymerization time was 15 minutes. 11.4 g of an ethylene/octene copolymer were isolated.

EXAMPLE 105

Polymerization using (tert-butylamido)dimethyl(1,3-dimethyl-5,6,7,8-tetrahydroindenyl)silane titanium dimethyl metal derivative Preparation of 4,5,6,7-tetrahydro-1-methyl-indan-3-one Cyclohexene (27.3 g, 0.33 mol), crotonic acid (28.7 g, 0.33 mol) and polyphosphoric acid (300 ml) were mechanically stirred under a nitrogen atmosphere at 60° C. for 30 minutes. The slurry was poured into water and the aqueous solution extracted with diethyl ether. The diethyl ether extract was washed successively with a 10 percent NaHCO$_3$ solution and a saturated NaCl solution. The organic extract was then dried over anhydrous MgSO4. The solution was then filtered and the solvent removed under reduced pressure. The crude product was then purified via vacuum distillation (bp 87°–92° C. at 5 mm) to give 32.6 g (66 percent) of purified material.

Preparation of 7,9 dimethylbicyclo-[4.3.0]-nona-1(6),7-diene

Methyl lithium (1.5M, 96 ml) was added dropwise to a solution of 4,5,6,7-tetrahydro-1-methyl-indan-3-one (17.7 g, 0.118 mol) in 50 ml of diethyl ether under an argon atmosphere whereupon the reaction mixture was refluxed for 18 hours. The mixture after this time period was hydrolyzed and the reaction mixture extracted with diethyl ether. The ether extracts were dried over anhydrous MgSO$_4$ and filtered. To the ether solution, 0.5 ml of 6M HCl was added and the solution stirred for one hour. After this time period the ether solution was washed with water, dried over anhydrous MgSO$_4$, filtered and concentrated. Distillation at reduced pressure afforded 8.0 g (45 percent) of product.

Preparation of lithium 1,3-dimethyl-5,6,7,8-tetrahydroindenide 7,9 dimethylbicyclo-[4.3.0]-nona-1(6),7-diene (5.0 g, 33.5 mmol) was added to 100 ml of pentane. To this solution n-BuLi in pentane (2.7M, 13 ml) was added dropwise and the mixture stirred for 12 hours. The resulting white precipitate was collected via filtration, washed with pentane and dried under reduced pressure to give 5.02 g (97 percent) of product.

Preparation of (N-t-butylamino)(dimethyl)(1,3-dimethyl-5,6,7,8-tetrahydroindenyl)silane 0.77 g of ClSiMe$_2$NHCMe$_3$ (4.67 mmol) was added to 50 ml of THF. To this solution 0.75 g (4.67 mmol) of lithium 1,3-dimethyl-5,6,7,8-tetrahydroindenide was added. The solution was then brought to reflux for 10 min and the solution was then cooled to room temperature. Gas-Chromatogram (GC) analysis showed the reaction to be complete. The solvent was then removed under reduced pressure, the residue extracted with pentane, filtered and the solvent again removed under reduced pressure to give 1.21 g of product (94 percent yield).

Preparation of dilithium (N-t-butylamido)(dimethyl)(1,3-dimethyl-5,6,7,8-tetrahydroindenyl)silane 1.21 g (4.36 mmol) of (N-t-butylamino)(dimethyl)(1,3-dimethyl-5,6,7,8-tetrahydroindenyl)silane were dissolved in 100 ml of diethylether. To this solution 5.72 ml (9.15 mmol) of nBuLi (1.6M in pentane) was added dropwise. Upon complete addition of the nBuLi the solution was stirred for 2 hours whereupon the solvent was removed under reduced pressure to give an oily yellow residue which solidified upon trituration with pentane to give 1.00 g (79 percent yield) of a tan solid product.

Preparation of [(N-t-butylamido)(dimethyl)(1,3-dimethyl-5,6,7,8-tetrahydroindenyl)silane]titanium dichloride ([(1,3-dimethyl-tetrahydroindenyl)SiMe$_2$N(t-Bu)]TiCl$_2$)

0.64 g (1.72 mmol) of TiCl$_3$(THF)$_3$ was dissolved in 75 ml of THF. To this solution 0.50 g (1.72 mmol) of dilithium (N-t-butylamido)(dimethyl)(1,3-dimethyl-5,6,7,8-tetrahydroindenyl)silane was added as a solid with stirring. The solution was then stirred for 45 min, after this time period PbCl$_2$ (0.239 g, 0.86 mmol) was added and the solution stirred for 45 minutes. The THF was then removed under reduced pressure. The residue was then extracted with toluene, the solution filtered and the toluene removed under reduced pressure. The residue was then triturated with pentane and the solution cooled to −20° C. for 3 hours. The product was collected via filtration and washed with cold pentane and dried under vacuum to yield 0.32 g (47 percent yield) of product.

Preparation of [(N-t-Butylamido)(dimethyl)(1,3-dimethyl-5,6,7,8-tetrahydroindenyl)silane]titanium dimethyl ([(1,3-dimethyl-tetrahydroindenyl)SiMe$_2$N(t-bu)]Ti(CH$_3$)$_2$)

0.32 g of (N-t-butylamido)(dimethyl)(1,3-dimethyl-5,6,7,8-tetrahydroindenyl )silane titanium dichloride (0.81 mmol) was suspended in 40 ml of Et$_2$O. To this suspension 0.56 ml of MeMgI (3.0M in diethyl ether) was added dropwise with stirring over a 20 minute period. Upon completion of the addition of the MeMgI, the solution was stirred for 40 minutes. After this time period the Et$_2$O was removed under reduced pressure and the residue extracted with pentane, the solution filtered and the filtrate evaporated to dryness under reduced pressure to give 0.21 g (73 percent yield) of product.

Polymerization

The procedure of example 103 was followed except that 0.50 micromoles of [(1,3-dimethyl-tetrahydroindenyl)SiMe$_2$N(t-Bu)]Ti(CH$_3$)$_2$ and 0.50 micromoles of the Lewis acid B(C$_6$F$_5$)$_3$, mixed in 2 mL of Isopar® E were used to form the catalyst/cocatalyst mixture. The reaction temperature was 120° C. 797 g of Isopar® E and 61 g of 1-octene are charged into the reactor and 20 Δpsi (0.14 ΔMPa) of hydrogen was added. The ethylene pressure was 500 psig (3.55 MPa). The polymerization time was 10 minutes. 29.2 g of an ethylene/octene copolymer were isolated. The micromelt index (I2), was 0.975.

EXAMPLE 106

The procedure of example 105 was followed except that 0.10 micromoles of [(1,3-dimethyl-tetrahydroindenyl)SiMe$_2$N(t-Bu)]Ti(CH$_3$)$_2$ and 0.10 micromoles of the Lewis acid, B(C$_6$F$_5$)$_3$ mixed in 2 mL of Isopar® E were used to form the catalyst mixture. The reaction temperature was 90° C. 715 g of Isopar® E and 143 g of 1-octene were charged into the reactor and 10 Δpsi (0.07 ΔMPa) of hydrogen was added. The ethylene pressure was 500 psig (3.45 MPa). The polymerization time was 10 minutes. 64.5 g of an ethylene/octene copolymer were isolated. The melt index (I2) was 0.346.

EXAMPLE 107

The procedure of example 106 was followed except that 0.025 micromoles of [(C$_5$Me$_4$)SiMe$_2$N(t-bu)]Ti(CH$_3$)$_2$ and 0.025 micromoles of the Lewis acid, B(C$_6$F$_5$)$_3$ mixed in 2 mL of Isopar® E were used to form the catalyst. The reaction temperature was 50° C. 679 g of Isopar® E and 179 g of 1-octene were charged into the reactor and 20 Δpsi (0.14 ΔMPa) of hydrogen was added. The ethylene pressure was 500 psig (3.55 MPa). The polymerization time was 60 minutes. 40.7 g of an ethylene/octene copolymer were isolated. The melt index, I2, was 0.166.

EXAMPLE 108

The procedure of example 107 was followed except that 2.00 micromoles of [(tetrahydrofluorenyl)SiMe$_2$N(t-Bu)]Ti(CH$_2$C$_6$H$_5$S)$_2$ (prepared by reacting [(N-t-butylamido)(dimethyl)tetrahydrofluorenyl)silane]titanium dichloride with benzyl magnesium chloride) and 2.00 micromoles of the the Lewis acid, B(C$_6$F$_5$)$_3$ mixed in 2 mL of Isopar® E were used to form the catalyst. The reaction temperature was 150° C. 822 g of Isopar® E and 36 g of 1-octene were charged into the reactor and 10 Δpsi (0.07 ΔMPa) of hydrogen was added. The ethylene pressure was 500 psig (3.55 MPa). The polymerization time was 15 minutes. 20.1 g of an ethylene/octene copolymer were isolated. The melt index, I2, was 0.327.

EXAMPLE 109

The procedure of example 108 was followed except that 2.00 micromoles of [(tetrahydrofluorenyl)-SiMe$_2$N(t-Bu)]Ti(CH$_2$C$_6$H$_5$)$_2$ and 2.00 micromoles of the Lewis acid, B(C$_6$F$_5$)$_3$ mixed in 2 mL of Isopar® E were used to form the catalyst The reaction temperature was 150° C. 822 g of Isopar® E and 36 g of 1-octene are charged into the reactor and 10 Δpsi (0.07 ΔMPa) of hydrogen was added. The ethylene pressure was 500 psig (3.55 MPa). The polymerization time was 15 minutes. 20.1 g of an ethylene/octene copolymer were isolated. The melt index, I2, was 0.327.

EXAMPLE 110

Polymerization using (n-tertbutylamido)dimethyl($\eta^5$-tertbutylcyclopentadienyl)silane titanium dimethyl metal derivative Lithium t-butylcyclopentadienide To a solution of 4.18 g (39.4 mmol) 6,6-dimethylfulvene in 80 mL diethylether at 0° C. were added 22.9 mL of a 1.72M (39.4 mmol) methyl lithium solution in ether. The resulting slurry was stirred several days, then filtered, washed with pentane and dried under vacuum.

(N-t-butylamino)(dimethyl)(t-butylcyclopentadienyl) silane

To a solution of 3.35 g (20.2 mmol) (N-t-butylamino)(chloro)dimethylsilane in 75 mL THF was added 3.58 g (17.7 mmol) lithium t-butylcyclopentadienide etherate. The reaction mixture was stirred several hours. The solvent was removed, the residue was extracted with pentane and filtered. The pentane was removed in vacuo to give the product as a pale yellow oil. The yield was 2.87 g, 64.6 percent.

Dilithium[(N-t-butylamido)(dimethyl)(t-butylcyclopentadienyl)silane

To a solution of 2.87 g (11.4 mmol) (N-t-butylamino)(dimethyl)(t-butylcyclopentadienyl)silane in 70 mL ether was added 15.8 mL of 1.48M (23.4 mmol) butyl lithium in hexane. The resulting clear solution was stirred overnight. The solvent was removed under reduced pressure. Yield was 107 percent of impure product.

[(N-t-butylamido)(dimethyl)(η-t-butylcyclopentadienyl)silane]titanium dichloride ([(t-butyl-C$_5$H$_3$)SiMe$_2$N(t-Bu)]TiCl$_2$)

In a flask were combined 0.60 g (2.27 mmol) dilithium[(N-t-butylamido)(dimethyl)(t-butylcyclopentadienyl)silane and 0.84 g (2.27 mmol) TiCl$_3$(THF)$_3$ as solids. To this was added 40 mL THF. The resulting dark violet solution was stirred for 10 minutes, then 0.35 g (1.25 mmol) PbCl$_2$ was added. The reaction mixture was stirred for less than one hour, the deep orange-brown reaction mixture was filtered, and the solvent removed under reduced pressure. The residue was extracted with pentane and the solution filtered and concentrated until solid material began to form. The slurry was cooled overnight in a freezer, the yellow product was collected on a frit, washed with pentane and dried under reduced pressure. The yield was 0.58 g, 69.6 percent.

[(N-t-butylamido)(dimethyl)(η-t-butylcyclopentadienyl)silane]titanium dimethyl ([(t-Butyl-C$_5$H$_3$)SiMe$_2$N(t-Bu)]Ti(CH$_3$)$_2$)

A 0.80 mL solution of 2.78M (2.22 mmol) methyl magnesium iodide in 15 mL ether was slowly added over 20 minutes to 0.41 g (1.11 mmol) [(N-t-butylamido)(dimethyl)(η-t-butylcyclopentadienyl)silane]titanium dichloride in 15 mL ether. The solution was stirred 20 minutes, then the solvent was removed. The residue was extracted with pentane and the resulting solution was filtered, then concentrated to an oil which crystallized on standing. Yield was 0.34 g, 94.6 percent.

Polymerization

The general polymerization procedure of Example 109 was followed using 0.25 micromoles of [(t-butyl-C$_5$H$_3$)SiMe$_2$N(t-Bu)]Ti(CH$_3$)$_2$ and 0.25 micromoles of the Lewis acid, B(C$_6$F$_5$)$_3$ mixed in 2 mL of Isopar® E were used to form the catalyst. The reaction temperature was 80° C. 1000 mL of Isopar® E, 100 g of propylene and 50 Δpsi (0.34 ΔMPa) of hydrogen were added. The ethylene pressure was 475 psig (3.38 MPa). The polymerization time was 10 minutes. 6.3 g of an ethylene/propylene copolymer was isolated. The melt index, I2, was 1.291. The density was 0.8868 g/mL.

EXAMPLE 111

Ethylene/norbornylene copolymer

The general polymerization procedure of Examples 109 was followed using 1.25 micromoles of [(C$_5$Me$_4$)SiMe$_2$N (t-Bu)]Ti(CH$_3$)$_2$ and 1.87 micromoles of the Lewis acid B(C$_6$F$_5$)$_3$ mixed in 2 mL of Isopar® E were used to form the catalyst. The reaction temperature was 140° C. 808 g of Isopar® E, 19.5 g of norbornene and 25 Δpsi (0.17 ΔMPa) of hydrogen were added. The ethylene pressure was 500 psig (3.55 MPa). The polymerization time was 10 minutes. 41.3 g of a random ethylene/norbornene copolymer was isolated. The melt index (I2) was 0.587. The polymer contained 2.38 weight percent norbornene as determined by $^{13}$C NMR.

EXAMPLE 112

Ethylene/norbornene copolymer

The procedure of example 111 was followed using 1.25 micromoles of [(C$_5$Me$_4$)SiMe$_2$N(t-Bu)]Ti(CH$_3$)$_2$ and 1.87 micromoles of the Lewis acid, B(C$_6$F$_5$)$_3$, mixed in 2 mL of Isopar® E to form the catalyst. The reaction temperature was 140° C. 758 g of Isopar® E, 39.0 g of norbornene and 25 Δpsi (0.17 ΔMPa) of hydrogen were added. The ethylene pressure was 500 psig (3.55 MPa). The polymerization time was 10 minutes. 38.1 g of a random ethylene/norbornene copolymer were isolated. The melt index (I2) was 1.52. The polymer contained 4.33 weight percent norbornene as determined by $^{13}$C NMR.

EXAMPLE 113

Ethylene/norbornene copolymer

The procedure of example 112 was followed using 2.00 micromoles of [(C$_5$Me$_4$)SiMe$_2$N(t-Bu)]Ti(CH$_3$)$_2$ and 3.00 micromoles of the Lewis acid, B(C$_6$F$_5$)$_3$, mixed in 2 mL of Isopar® E to form the catalysts/cocatalyst mixture. The reaction temperature was 50° C. 1200 mL of a solution containing 334.6 g of norbornene in Isopar® E and 5 Δpsi (0.03 ΔMPa) of hydrogen were added. The ethylene pressure was 100 psig (0.79 MPa). The polymerization time was 30 minutes. 22.9 g of a random ethylene/norbornene copolymer were isolated. The melt index, I2, was 1.43. The polymer contained 73.78 weight percent norbornene as determined by $^{13}$C NMR. The polymer Tg was 83.8° C.

EXAMPLE 114

Polymerization using phenyl bis(perfluorophenyl)borane Lewis acid

Preparation of B(C$_6$F$_5$)$_2$(C$_6$H$_5$)

A 250 mL flask was evacuated, cooled to −78° C. and charged with 120 mL of mixed hexane solvent, vacuum transferred from sodium benzophenone ketyl. The flask was backfilled with argon, to 0.11 MPa pressure, and bromopentafluorobenzene (deoxygenated by sparging with nitrogen, 10.00 grams, 40.5 mmol) was added via a syringe. Agitation of the mixture was begun (magnetic stir bar), giving a clear, colorless solution, to which was added n-butyllithium (16.2 mL of 2.5M hexane solution, 40.5 mmol) via syringe. As the n-butyllithium solution was added, a clear colorless solid separated from the mixture. This slurry was allowed to stir at −78° C. for 70 minutes and then dichlorophenylboron (3.22 g, 20.3 mmol, 0.50 equivalents) was added from a syringe. After stirring for an additional 30 minutes at −78° C., no change was noted and the mixture were allowed to warm to ambient temperature. As the mixture warmed, a thick white precipitate formed. After stirring at 22° C. for 15 minutes the flask was opened to vacuum and the volume of the mixture was reduced to 50 mL. The mixture was filtered, the solid extracted with three 20 mL portions of mixed hexane solvent and the filtrate was reduced to 20 mL under reduced pressure. The resulting solution was cooled to −78° C., giving a very thick slurry of colorless, crystalline solid.

The slurry was thinned by addition of 20 mL of hexane. The solid was collected by filtration and dried under reduced pressure. Yield was 4.86 g, 57 percent.

Polymerization

The polymerization procedure of examples 3–37 was followed except that 850 mL of Isopar® E is added to the reactor followed by 20 g of propylene. 25 Δpsi (0.17 ΔMPa) of hydrogen were then added and the solution heated to 130° C. The solution was then saturated with ethylene at 500 psig (3.55 MPa). 10 micromoles of the metal complex [(C$_5$Me$_4$)SiMe$_2$N(t-Bu)]TiMe$_2$ and 10 micromoles of the Lewis acid, B(C$_6$F$_5$)$_2$(C$_6$H$_5$), were mixed in 2 mL of Isopar® E and this solution was transferred into the reactor to begin the polymerization. The reaction was allowed to proceed for 15 minutes with ethylene being supplied on demand at 500 psig (3.55 MPa). 2.8 g of an ethylene/propylene copolymer were obtained. The melt index, I$_2$, was 7.52.

EXAMPLE 115

Ethylene/ethylidenenorbornene copolymer

The procedure of example 111 was followed using two consecutive additions of a catalyst solution prepared by mixing 5.0 micromoles of [C$_5$Me$_4$)SiMe$_2$N(t-Bu)]Ti(CH$_3$)$_2$ and 5.0 micromoles of the Lewis acid, B(C$_6$F$_5$)$_3$, mixed in 2 mL of Isopar® E. The reaction temperature was 130° C. 1200 mL of a solution containing 50 mL of 5-ethylidene-2-norbornene in Isopar® E and 50 psi (0.34 ΔMPa) hydrogen were added. The ethylene pressure was 475 psig (3.38 MPa). The polymerization time was 20 minutes. 59.9 g of an ethylene/5-ethylidene-2-norbornene copolymer was isolated. The melt index, I2, was 1.55. The polymer contains 9.06 weight percent 5-ethylidene-2-norbenene as determined by $^{13}$C NMR.

EXAMPLE 116

Various Lewis acids are tested for Lewis acidity for use in preparation of catalysts according to the present invention. Acidity values and the techniques employed in determining such values are contained in Table V.

TABLE V

| Run | Lewis Acid | Acidity (Kcal/mole) | Base |
|---|---|---|---|
| 1 | phenylbis(perfluorophenyl)borane | 0.0[1,2,3] | CH$_3$— or NH$_3$ |
| 2 | tris(2,3,5,6-tetrafluorophenyl)borane | −2.1[2] | CH$_3$— |
| 3 | tris(3,4,5-trifluorophenyl)borane | −5.2[1] | " |
| 4 | tris(3,4,5-trifluorophenyl)aluminum | −11.2[2] | " |
| 5 | tris(1,2,2-trifluoroethenyl)borane | −12.3[1] | " |
| 6 | tris(2,3,4,5-tetrafluorophenyl)borane | −15.2[2] | " |
| 7 | tris(perfluorophenyl)borate[4] | −17.5[1] | " |
| 8 | tris(perfluorophenyl)borane | −17.8[1,5] | " |
| 9 | 1,3,5-cyclohexanetriol borate | −22.2[1] | NH$_3$ |
| 10 | 1,1,1-trimethylolethane borate | −25.1[1] | " |

[1]HF/3-21 g method
[2]AM1 method
[3]Lewis acidity according to Childes' technique, Δδ, is 0.77 ppm. Relative acidity = 0.0 ppm
[4]B(OC$_6$F$_5$)$_3$
[5]Lewis acidity according to Childes' technique, Δδ, is 1.10 ppm. Relative acidity = 0.33 ppm

We claim:

1. A process for preparing a catalyst having a limiting charge separated structure corresponding to the formula:

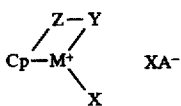

wherein:
Cp is a cyclopentadienyl group or a substituted derivative thereof that is π-bound to M wherein each substituent is independently selected from the group consisting of $C_{1-20}$ hydrocarbyl radicals, $C_{1-20}$ halogenated hydrocarbyl radicals, $C_{1-20}$ hydrocarbyl substituted metalloid radicals wherein the metalloid is selected from Group 14 of the Periodic Table of the Elements, and halogen radicals; or two or more such radicals may together with Cp form a fused ring system;

Z is a divalent moiety comprising oxygen, boron, or a member of Group 14 of the Periodic Table of the Elements;

Y is a ligand group comprising nitrogen, phosphorus, oxygen or sulfur or optionally Z and Y together form a fused ring system;

M is a metal of Group 4 or the Lanthanide series of the Periodic Table of the Elements;

X independently each occurrence is hydride or a hydrocarbyl, silyl or germyl group said X having up to 20 carbon, silicon or germanium atoms; and A⁻ is an anion of a Lewis acid, A, having relative Lewis acidity greater than or equal to that of phenylbis(perfluorophenyl)borane, said anion being compatible with the metal cation, the steps of the process comprising contacting a derivative of a Group 4 or Lanthanide metal corresponding to the formula:

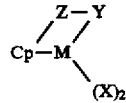

wherein
Cp, Z, Y, M, and X are as previously defined herein,
with the Lewis acid, A, under conditions to cause abstraction of X and formation of the anion XA⁻.

2. A process for preparing an addition polymerization catalyst having a limiting, charge separated structure of the formula:

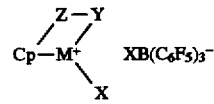

wherein:
Cp is a cyclopentadienyl group or a substituted derivative thereof that is π-bound to M wherein each substituent is independently selected from the group consisting of $C_{1-20}$ hydrocarbyl radicals, $C_{1-20}$ halogenated hydrocarbyl radicals, $C_{1-20}$ hydrocarbyl substituted metalloid radicals wherein the metalloid is selected from Group 14 of the Periodic Table of the Elements, and halogen radicals; or two or more such radicals may together with Cp form a fused ring system;

Z is a divalent moiety comprising oxygen, boron, or a member of Group 14 of the Periodic Table of the Elements;

Y is a ligand group comprising nitrogen, phosphorus, oxygen or sulfur or optionally Z and Y together form a fused ring system;

M is a metal of Group 4 or the Lanthanide series of the Periodic Table of the Elements; and X independently each occurrence is hydride or a hydrocarbyl, silyl or germyl group, said X having up to 20 carbon, silicon or germanium atoms;

the steps of the process comprising contacting a derivative of a Group 4 or Lanthanide metal corresponding to the formula:

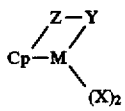

wherein
Cp, Z, Y, M, and X are as previously defined herein,
with tris(pentafluorophenyl)borane under conditions to cause abstraction of X and formation of the anion, ⁻XB(C₆F₅)₃.

3. A process as claimed in claim 1 wherein M is a titanium or zirconium.

4. A process as claimed in claim 1, wherein the metal derivative is an amidosilanediyl- or amidoalkanediyl-compound corresponding to the formula:

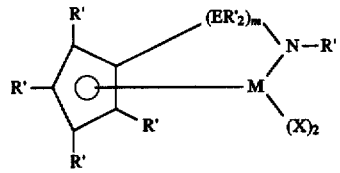

wherein:
M is titanium or zirconium;
R' each occurrence is independently selected from hydrogen, silyl, alkyl, aryl and combinations thereof said R' having up to 20 carbon or silicon atoms, and optionally two or more R' groups on the cyclopentadienyl group together with the cyclopentadienyl group may form a fused ring system;
E is silicon or carbon;
m is one or two; and
X independently each occurrence is hydride, alkyl, aryl, or halogen substituted aryl said X group having up to 20 carbons.

5. A process as claimed in claim 4, wherein X is hydride or $C_1$–$C_{10}$ hydrocarbyl.

6. A process as claimed in claim 1 wherein the Lewis acid is a boron compound lacking in halogen moieties directly attached to the boron.

7. A process as claimed in claim 6, wherein the Lewis acid is selected from the group consisting of tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(1,2,2-trifluoroethenyl)borane, phenylbis(perfluorophenyl)borane, tris(3,4,5-trifluorophenyl)aluminum, tris(perfluorophenyl)borate, 1,3,5-cyclohexanetriol borate, and 1,1,1-trimethylolethane borate.

8. A process as claimed in claim 2, wherein each X independently is hydride, alkyl or aryl of up to 10 carbon atoms; Y is NR'; and Z is $(ER'_2)_m$, wherein each R' independently is hydrogen, silyl, alkyl, aryl or a combination thereof having up to 10 carbon or silicon atoms, and E is silicon or carbon; and m is 1 or 2.

9. A process as claimed in claim 8, wherein X is hydride or $C_1$–$C_{10}$ hydrocarbyl.

10. A process as claimed in claim 2, wherein M is titanium or zirconium.

* * * * *